US011337741B2

(12) United States Patent
Lenchig (10) Patent No.: US 11,337,741 B2
(45) Date of Patent: May 24, 2022

(54) LATERALLY DEPLOYED KYPHOPLASTY BALLOON TAMPONADE

(71) Applicant: Sergio Lenchig, Fort Lauderdale, FL (US)

(72) Inventor: Sergio Lenchig, Fort Lauderdale, FL (US)

(*) Notice: Subject to any disclaimer, the term of this patent is extended or adjusted under 35 U.S.C. 154(b) by 138 days.

(21) Appl. No.: 16/865,030

(22) Filed: May 1, 2020

(65) Prior Publication Data
US 2021/0338298 A1 Nov. 4, 2021

(51) Int. Cl.
*A61B 17/88* (2006.01)
*A61M 25/10* (2013.01)

(52) U.S. Cl.
CPC . *A61B 17/8855* (2013.01); *A61M 2025/1079* (2013.01)

(58) Field of Classification Search
CPC ............ A61B 17/8855; A61B 17/8858; A61B 17/8852; A61B 17/885; A61M 2025/1079; A61M 2025/1084
See application file for complete search history.

(56) References Cited

U.S. PATENT DOCUMENTS

| 5,100,385 A | 3/1992 | Bromander |
| 6,623,452 B2 | 9/2003 | Chien et al. |
| 8,734,459 B1 | 5/2014 | Alobaid |
| 8,900,304 B1 | 12/2014 | Alobaid |
| 8,939,977 B2 | 1/2015 | DiPoto et al. |
| 9,149,318 B2 | 10/2015 | Druma |
| 9,510,885 B2 | 12/2016 | Burger et al. |
| 9,554,840 B2 | 1/2017 | Druma et al. |
| 9,687,281 B2 | 6/2017 | Dipoto et al. |
| 10,219,910 B2 | 3/2019 | McCormack |
| 10,238,443 B2 | 3/2019 | Seifert et al. |
| 10,342,498 B2 | 7/2019 | Smith et al. |
| 10,413,338 B2 | 9/2019 | Anderson et al. |
| 2007/0010845 A1* | 1/2007 | Gong ................. A61B 17/8855 606/192 |
| 2009/0299327 A1* | 12/2009 | Tilson .................. A61M 29/02 604/99.04 |
| 2009/0299374 A1* | 12/2009 | Tilson ............... A61M 25/1002 606/94 |
| 2012/0065694 A1 | 3/2012 | Simonson |

(Continued)

FOREIGN PATENT DOCUMENTS

| CN | 103284782 A | 9/2013 |
| EP | 3322366 A4 | 3/2019 |

(Continued)

*Primary Examiner* — Zade Coley
*Assistant Examiner* — Diana Jones
(74) *Attorney, Agent, or Firm* — Mark Terry (57) ABSTRACT

A medical device for kyphoplasty procedures is disclosed. The medical device includes a trocar configured for insertion in a vertebral cavity, the trocar having a longitudinal axis that is perpendicular to a second axis, an orifice at a first end of the trocar in, the orifice configured for deploying a balloon tamponade, the balloon tamponade configured for inserting into a second end of the trocar, through the trocar and out of the orifice at a first end of the trocar, and, wherein the balloon tamponade is configured to be inflated such that the balloon tamponade inflates to a greater extent along the second axis than the longitudinal axis of the trocar.

18 Claims, 11 Drawing Sheets

(56) References Cited

U.S. PATENT DOCUMENTS

| | | |
|---|---|---|
| 2012/0165732 A1 | 6/2012 | Muller |
| 2013/0325036 A1 | 12/2013 | Bonutti |
| 2014/0276572 A1* | 9/2014 | Auyoung ........... A61B 17/8855 606/92 |
| 2015/0335866 A1* | 11/2015 | Stapleton .............. A61M 25/10 604/103.1 |
| 2017/0196508 A1 | 7/2017 | Hunter |
| 2018/0085150 A1 | 3/2018 | O'Halloran et al. |
| 2018/0125365 A1 | 5/2018 | Hunter et al. |
| 2018/0193064 A1 | 7/2018 | Kim |
| 2018/0199977 A1 | 7/2018 | Nash |
| 2019/0201066 A1* | 7/2019 | Sasaki ................ A61B 17/8811 |
| 2019/0357955 A1* | 11/2019 | Chan ................. A61B 17/8811 |

FOREIGN PATENT DOCUMENTS

| | | |
|---|---|---|
| EP | 2361046 B1 | 4/2019 |
| JP | 2009285135 A | 12/2009 |
| JP | 6066930 B2 | 1/2017 |
| KR | 101721279 B1 | 3/2017 |
| WO | 2017120313 A1 | 7/2017 |

* cited by examiner

LATERALLY DEPLOYED KYPHOPLASTY BALLOON TAMPONADE

CROSS-REFERENCE TO RELATED APPLICATIONS

Not applicable.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISC

Not applicable.

TECHNICAL FIELD

The present invention relates to the field of minimally invasive surgeries, and more specifically to kyphoplasty surgeries for restoring the height and angle of kyphosis of a fractured vertebra.

BACKGROUND

Kyphoplasty is a minimally invasive spinal surgery in which bone cement is injected through a small hole in the skin into a fractured vertebra to try to relieve back pain caused by a vertebral compression fracture. Kyphoplasty restores the height and angle of kyphosis of a fractured vertebra, followed by its stabilization using injected bone cement. The procedure typically includes the use of a small balloon, also called a balloon tamponade, that is inflated in the vertebral body to create a void within the cancellous bone prior to cement delivery. Once the void is created, the bone cement is delivered directly into the newly created void.

FIGS. 1-8 depict the presently known process of treating spinal compression fractures using the prior art kyphoplasty procedure 100. The drawings provide both top and side views of the tools commonly used in the kyphoplasty procedure and the processes associated with their use.

Figure 1:
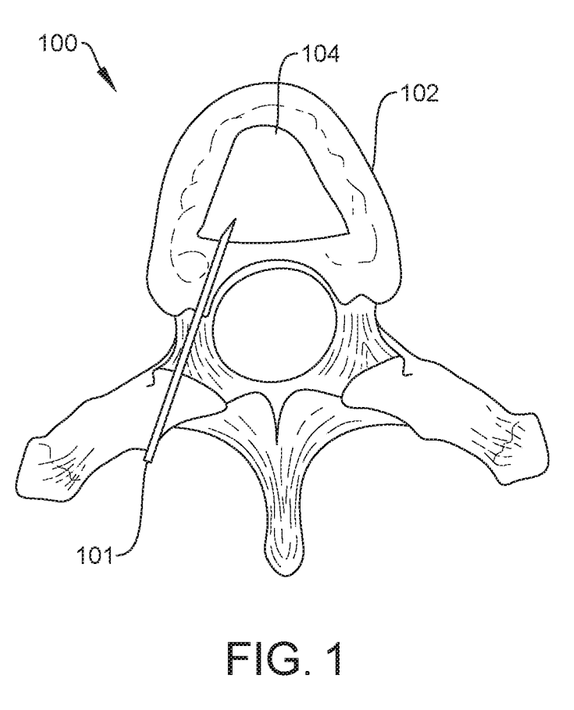
FIG. 1 is a top view of a vertebra undergoing a prior art kyphoplasty procedure.
Figure 2:
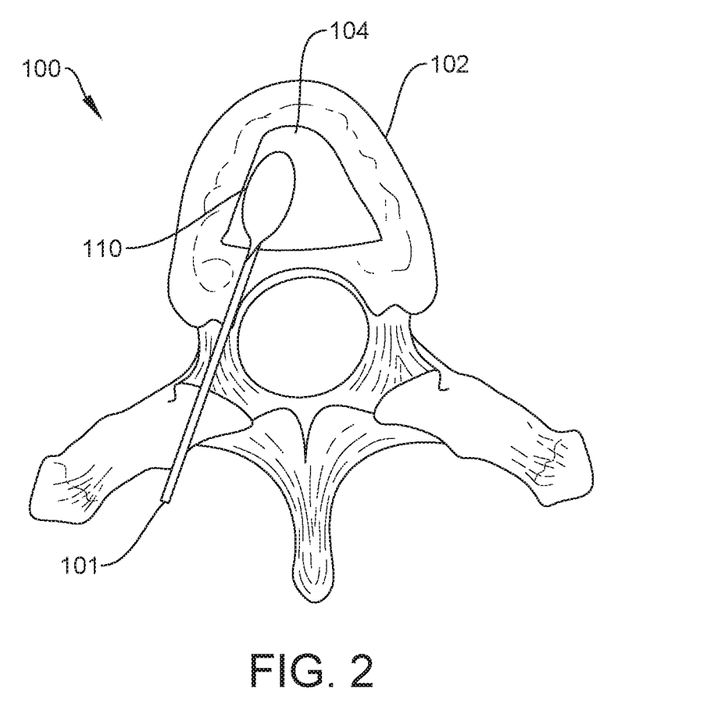
FIG. 2 is a top view of a vertebra undergoing a prior art kyphoplasty procedure, wherein the balloon tamponade has been inserted into the vertebral cavity.
Figure 3:
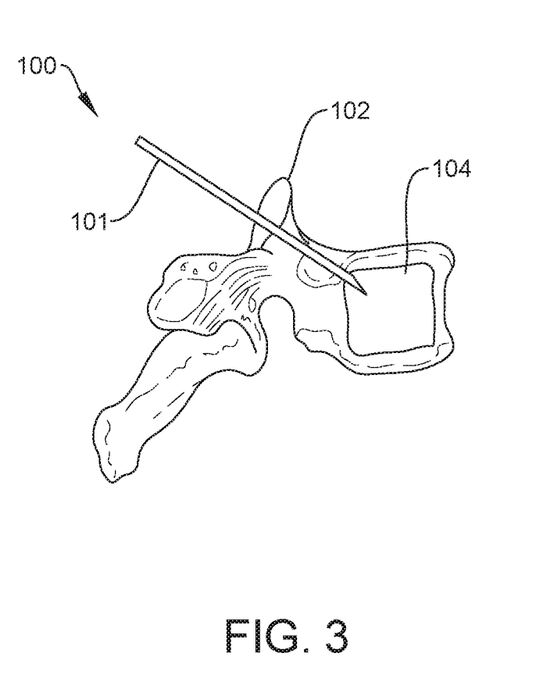
FIG. 3 is a side view of a vertebra undergoing a prior art kyphoplasty procedure.
Figure 4:
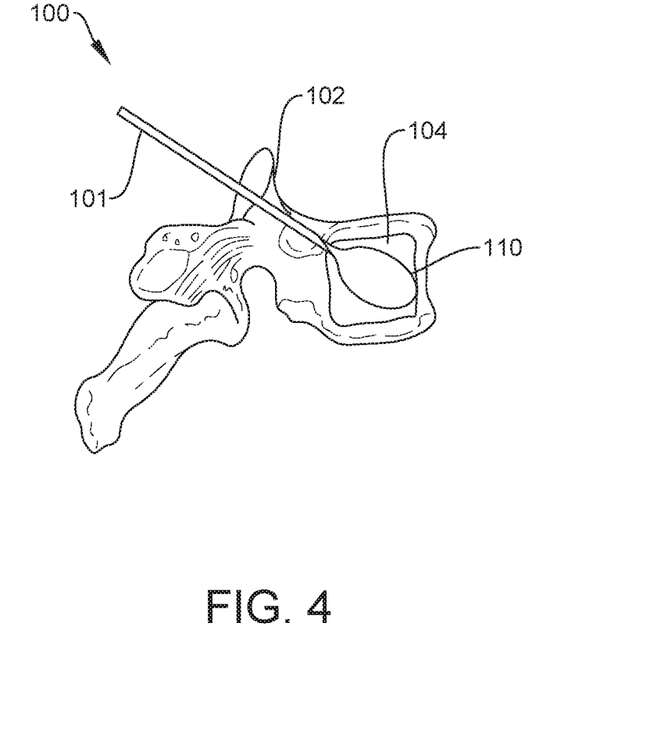
FIG. 4 is a side view of a vertebra undergoing a prior art kyphoplasty procedure, wherein the balloon tamponade has been inserted into the vertebral cavity.

FIG. 1 is a top view of a single vertebra 102. In FIG. 1, a trocar, or narrow hollow tube, 101 has been inserted into the vertebral cavity 104 of the vertebra 102. Typically, in a prior art kyphoplasty procedure 100, the patient will undergo radiography (using X-rays, gamma rays, or similar ionizing radiation and non-ionizing radiation), such that the surgeon can monitor the placement of the trocar inside the patient. FIG. 2 shows that once the trocar has been inserted, a balloon tamponade 110 is inserted into the vertebral cavity 104 through the trocar. The balloon tamponade 110 is inflated once it is inside of the vertebral cavity 104, as shown in FIG. 2. The inflation of the balloon tamponade restructures the body of the vertebra, creating, or re-creating, a vertebral cavity therein. FIGS. 3 and 4 are side views of the same process, wherein FIG. 3 shows the hollow tube, or trocar, 101 being inserted into the vertebral cavity 104 of the vertebra 102. FIG. 4 depicts the inflated balloon tamponade 110 inside the vertebral cavity 104, restructuring the formerly collapsed, or fractured, vertebral cavity.

Once the inflated balloon tamponade 110 has caused the body of the vertebra to take the desired structure, the balloon tamponade is then deflated and removed from the vertebral cavity 104, leaving the cavity momentarily empty. In order to prevent additional collapse or compression, the empty vertebral cavity 104 is quickly filled with orthopedic cement fed through the hollow tube, or trocar. Once the cement is in place, the trocar is removed to allow the cement to take the form of the cavity and harden therein.

Figure 5:
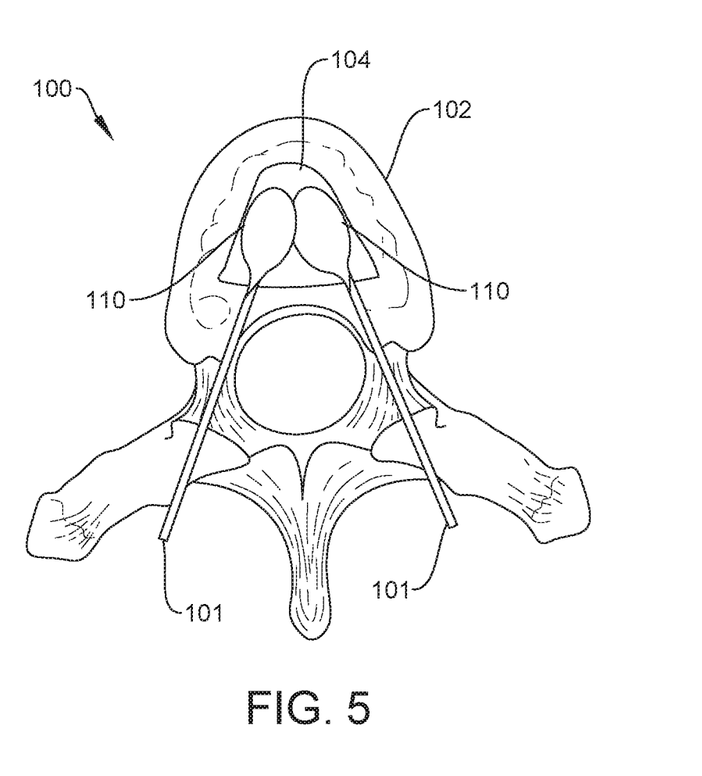
FIG. 5 is a top view of a vertebra undergoing a prior art kyphoplasty procedure, wherein two balloon tamponades, side by side, have been inserted into the vertebral cavity.

Due to the size of the vertebral cavity 104 and the manner in which the prior art balloon tamponade 110 is inflated and placed in the vertebral cavity, two balloon tamponades 110, side-by-side, may be required in order to appropriately address the compression fracture, as shown in FIG. 5 (also a top view). In said situations, two separate balloon tamponades 110 (one on the left side and one on the right side) is inserted into the vertebral cavity 104 through the trocar. Both balloon tamponades are inflated once inside of the vertebral cavity 104 to ensure that the body of the vertebra 102 is fully restructured. Once the compressed vertebra takes the desired structure, both balloon tamponades 110 and trocars 101 are removed and the vertebral cavity 104 is filled with orthopedic cement.

One of the problems associated with the use of two or more balloon tamponades is the increase in complications associated with making multiple incisions in the patient to insert a trocar. It is desirable to minimize the number of incisions made in the patient, so as to lower the incidence of infections, longer recovery times or other complications associated with more incisions. Another problem associated with the use of two or more balloon tamponades is the increase in complications associated with inserting multiple medical instruments and devices into the patient. It is optimal to minimize the number of medical instruments and devices inserted into the patient, in order to reduce the chances of said instruments being left behind in the patient or accidentally causing collateral damage to other organs or tissues.

As a result, there exists a need for improvements over the prior art and more particularly, for more efficient methods and systems for effectuating minimally invasive kyphoplasty surgeries.

SUMMARY

A medical device for kyphoplasty procedures is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a medical device for kyphoplasty procedures is disclosed. The medical device includes a trocar configured for insertion in a vertebral cavity, the trocar having a longitudinal axis that is perpendicular to a second axis, an orifice at a first end of the trocar, the orifice configured for deploying a balloon tamponade, the balloon tamponade configured for inserting into a second end of the trocar, through the trocar and out of the orifice at the first end of the trocar, and, wherein the balloon tamponade is configured to be inflated such that the balloon tamponade inflates to a greater extent along the second axis than the longitudinal axis of the trocar.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the invention and together with the description, serve to explain the principles of the disclosed embodiments. The embodiments illustrated herein are presently preferred, it being understood, however, that the invention is not limited to the precise arrangements and instrumentalities shown, wherein.

DETAILED DESCRIPTION

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the prior art by providing a more efficient method and system for effectuating minimally invasive kyphoplasty surgeries. The disclosed embodiments are designed to reduce or eliminate complications associated with making multiple incisions in the patient to insert a trocar. The disclosed embodiments minimize the number of incisions made in the patient in a kyphoplasty procedure, thereby lowering the incidence of infections, reducing recovery times and reducing complications associated with more incisions. The disclosed embodiments are also configured to decrease complications associated with inserting multiple medical instruments and devices into the patient. The disclosed embodiments minimize the number of medical instruments and devices inserted into the patient in a kyphoplasty procedure, thereby reducing the chances of said instruments being left behind in the patient or accidentally causing collateral damage to other organs or tissues.

Figures 6, 7, 8:
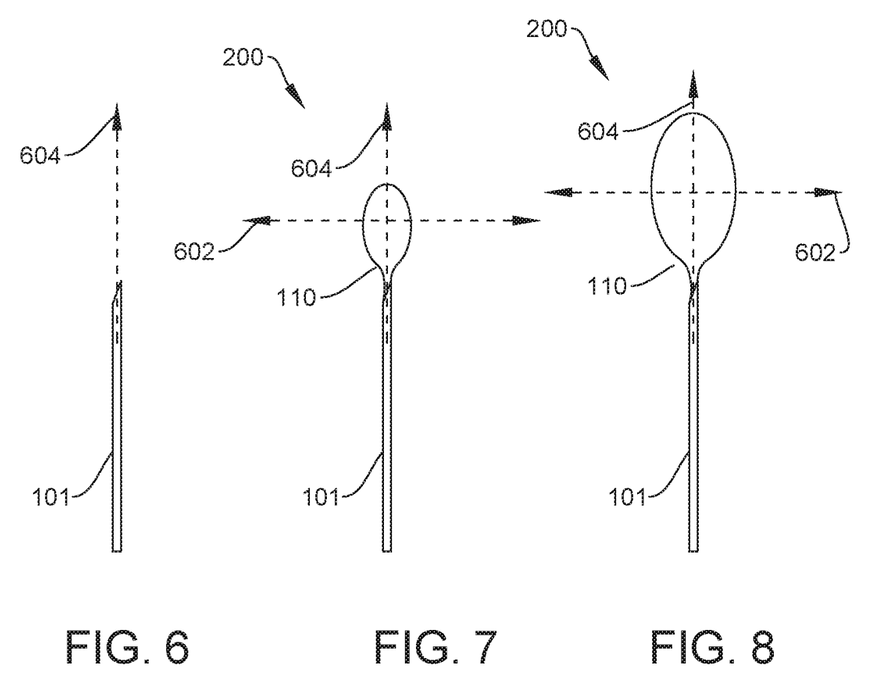
FIG. 6 is a side view of a prior art trocar used for a kyphoplasty procedure.
FIG. 7 is a side view of a prior art trocar and partially inflated balloon tamponade used for a kyphoplasty procedure.
FIG. 8 is a side view of a prior art trocar and fully inflated balloon tamponade used for a kyphoplasty procedure.

Referring now to the Figures, FIGS. 6, 7, and 8 are drawings depicting the process of inflating a prior art balloon tamponade 110 through the hollow tube, or trocar, 101. The prior art system 200 includes a prior art balloon tamponade 110 and the hollow tube, or trocar, 101. FIG. 6 shows the trocar placed along a vertical axis 604. FIG. 6 does not yet show a balloon tamponade. FIG. 7 shows the same trocar 101, modified to further depict a balloon tamponade 110 beginning to expand along the vertical axis 604 and a horizontal axis 602. FIG. 8 shows the same trocar 101, modified to further depict a balloon tamponade 110 fully expanded along the vertical axis 604 and a horizontal axis 602. The balloon tamponade 110 is inflated until being of sufficient size such that that the vertebral body takes the desired structure. Note in FIG. 8 that the balloon tamponade 110 has expanded to a greater extent along the vertical axis 604, and to a lesser extent along the horizontal axis 602. For this reason (i.e., expansion of the balloon tamponade along the vertical axis greater than the horizontal axis), and due to the nature of how the trocars 101 are inserted into the vertebral cavity 104, two balloon tamponades 110, side-by-side, are required to adequately fill the vertebral cavity 104, as shown in FIG. 5.

Referring now to the Figures, FIGS. 9-16 illustrate an improved trocar and fully inflated balloon tamponade used for a kyphoplasty procedure, according to an example embodiment. The claimed system 900 includes an improved balloon tamponade 910 and the hollow tube, or trocar, 901. The trocar 901 may include an orifice 1010 (see FIG. 10) at or near a first end of the trocar, the orifice configured for deploying a balloon tamponade. In one embodiment, the orifice 1010 may be located a specified distance from the distal end of the trocar, wherein the orifice 1010 is located closer to the distal end of the trocar than the proximal end.

Figure 9:
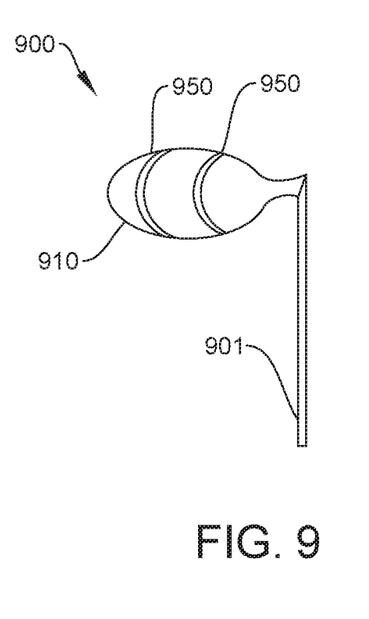
FIG. 9 is a side view of an improved trocar and fully inflated balloon tamponade used for a kyphoplasty procedure, according to an example embodiment.

FIG. 9 is a side view of the improved trocar 901 and fully inflated balloon tamponade 910 used for a kyphoplasty procedure, according to an example embodiment. FIG. 9 shows that the inflated balloon tamponade 910 expands laterally, or horizontally, with respect to a vertical trocar 901. In other words, during deployment, the inflated balloon tamponade 910 expands mainly along an axis that is orthogonal or perpendicular to a longitudinal axis of the trocar 901. Note that the balloon tamponade 910 includes two vertical stripes or indicators 950 that wrap vertically around the balloon, similar to lines of longitude on a globe. Each vertical stripe or indicator 950 is composed of radiopaque material.

Radiopacity is opacity to the radio wave and X-ray portion of the electromagnetic spectrum. Radiopacity is the relative inability of said types of electromagnetic radiation to pass through a particular material. Materials that inhibit the passage of electromagnetic radiation are called radiopaque. Radiopaque volumes of material have white appearance on radiographs, compared with the relatively darker appearance of radiolucent volumes. Radiopacity can also be quantified according to the Hounsfield scale. In modern medicine, radiopaque substances are those that will not allow X-rays or similar radiation to pass. Two common radiopaque elements used in medical imagery are barium and iodine. Additional examples of radiopaque materials include titanium, tungsten, barium sulfate, and zirconium oxide.

The radiopacity of the vertical stripes or indicators 950 is used during radiological intervention. The radiopacity of the vertical stripes or indicators 950 is important since it allows the balloon tamponade to be tracked during the interventional procedure wherein the balloon tamponade is positioned and inflated. This allows the surgeon to monitor the position of the balloon tamponade when it is inserted into the vertebral cavity and inflated.

The vertical stripes or indicators 950 may comprise radiopaque material that is deposited in vertical stripes on the exterior surface of the balloon tamponade 910. Alternatively, the vertical stripes or indicators 950 may comprise radiopaque material that is deposited in vertical stripes on the interior surface of the balloon tamponade 910. In another embodiment, the vertical stripes or indicators 950 may comprise radiopaque material that is integrated, or embedded, in the material composition of the balloon tamponade 910 when the balloon tamponade is manufactured.

Figures 10, 11:
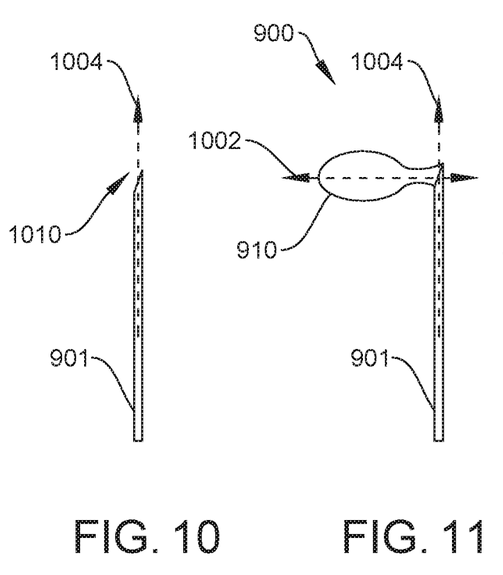
FIG. 10 is a side view of the improved trocar used for a kyphoplasty procedure, according to an example embodiment.
FIG. 11 is a side view of the improved trocar and partially inflated balloon tamponade used for a kyphoplasty procedure, according to an example embodiment.
Figure 12:
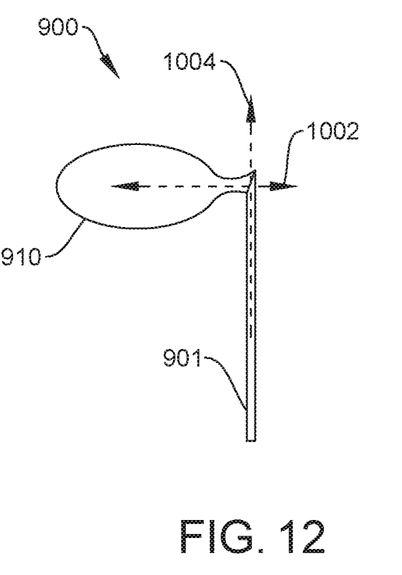
FIG. 12 is a side view of the improved trocar and fully inflated balloon tamponade used for a kyphoplasty procedure, according to an example embodiment.
Figure 13:
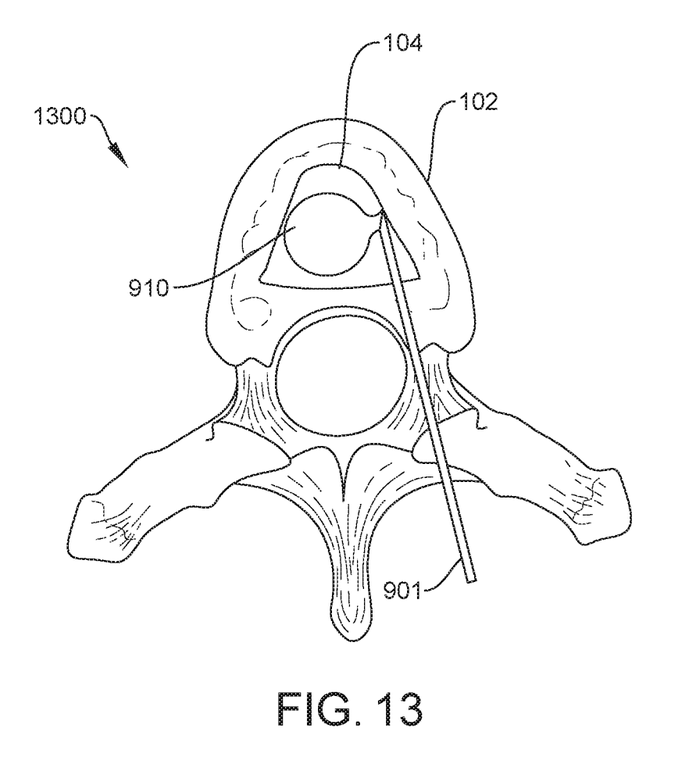
FIG. 13 is a top view of a vertebra undergoing a kyphoplasty procedure, wherein the improved balloon tamponade has been inserted into the vertebral cavity, according to an example embodiment.

Referring now to FIGS. 10, 11, and 12 are drawings depicting the process of inflating the improved balloon tamponade 910 through the hollow tube, or trocar, 901. The claimed system 900 includes the improved balloon tamponade 910 and the hollow tube, or trocar, 901. FIG. 10 shows the trocar placed along a vertical axis 1004, which trocar includes an orifice at or near the distal, or working, end of the trocar. FIG. 10 does not yet show a balloon tamponade. FIG. 11 shows the same trocar 901, modified to further depict the balloon tamponade 910 beginning to expand (via the orifice) only slightly along the vertical axis 1004 and mostly along a horizontal axis 1002. FIG. 12 shows the same trocar 901, modified to further depict the balloon tamponade 910 fully expanded along both vertical and horizontal axes 1004 and 1002. The balloon tamponade 910 is inflated until being of sufficient size such that the vertebral body takes the desired structure. Note in FIG. 12 that the balloon tamponade 910 has expanded to a greater extent along the horizontal axis 1002, and to a lesser extent along the vertical axis 1004. For this reason (i.e., expansion of the balloon tamponade along the horizontal axis greater than the vertical axis), and due to the nature of how the trocar 901 is inserted into the vertebral cavity 104, only one balloon tamponade 910 is required to adequately fill the vertebral cavity 104, as shown in FIG. 13. Note that FIG. 13 is a top view of a vertebra 102 undergoing a kyphoplasty procedure 1300, according to an example embodiment. FIG. 12 illustrates the benefit of the claimed embodiments, which is the use of only one balloon tamponade in a kyphoplasty procedure (as opposed to two or more), the making of only one incision and a resulting savings in time, medical expenditure and patient recovery.

Figure 14:
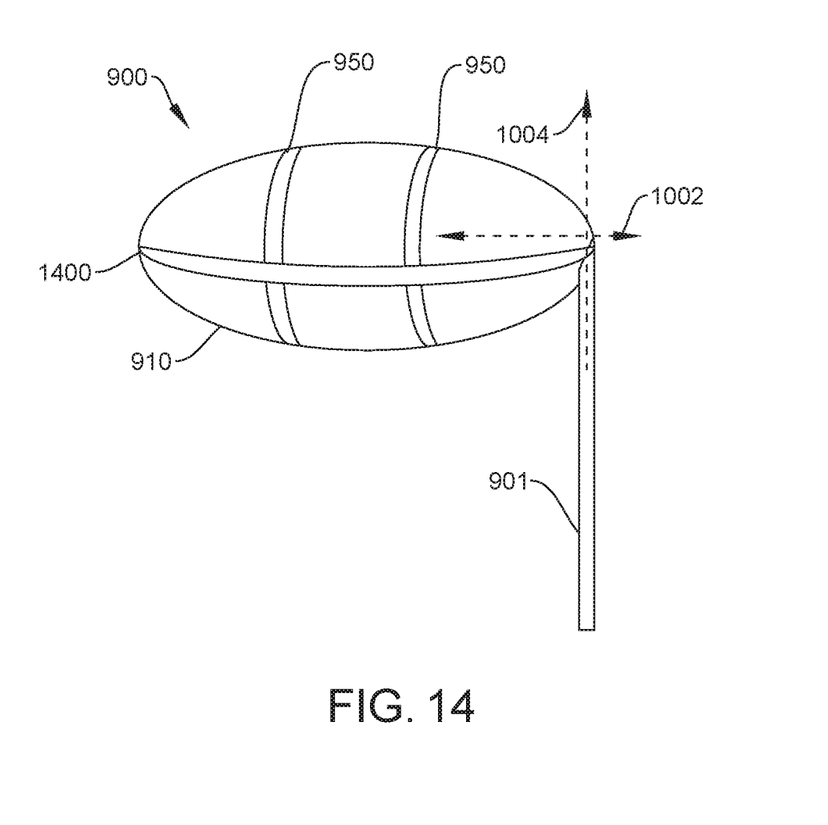
FIG. 14 is another side view of an improved trocar and fully inflated balloon tamponade used for a kyphoplasty procedure, according to an example embodiment.

FIG. 14 is another side view of an improved trocar 901 and fully inflated balloon tamponade 910 used for a kyphoplasty procedure 1300, according to an example embodiment. Note that the balloon tamponade 910 includes two vertical stripes or indicators 950 that wrap vertically around the balloon, similar to lines of longitude on a globe. Note also that the balloon tamponade 910 includes at least one horizontal stripe or indicator 1400 that wraps horizontally around the balloon, similar to lines of latitude on a globe. Each stripe or indicator 950, 1400 is composed of radiopaque material, which aids the surgeon in monitoring the position of the balloon tamponade 910 when it is inserted into the vertebral cavity and inflated.

The stripes or indicators 950, 1400 may comprise radiopaque material that is deposited in vertical stripes on the exterior surface of the balloon tamponade 910. Alternatively, the stripes or indicators 950, 1400 may comprise radiopaque material that is deposited in vertical stripes on the interior surface of the balloon tamponade. In another embodiment, the stripes or indicators 950, 1400 may comprise radiopaque material that is integrated, or embedded, in the material composition of the balloon tamponade when the balloon tamponade is manufactured.

FIG. 14 shows the lateral deployment of the balloon tamponade 910, which expands horizontally (axis 1002), with respect to a vertical trocar 901. That is, the balloon tamponade 910 is inflated such that, during deployment, it expands mainly along an axis 1002 that is orthogonal or perpendicular to a longitudinal axis 1004 of the trocar 901.

The balloon tamponade 910 and its components may be manufactured from a variety of materials including rubber, plastic, fabric, carbon fiber, epoxy resin, graphite, or any combination of the above. Rubber includes natural rubber, synthetic rubber, latex, styrene butadiene rubber, butyl, nitrile, neoprene, ethylene propylene diene monomer, silicone, viton, polyurethane, hydrogenated nitrile and the like. Plastic covers a range of synthetic or semi-synthetic polymerization products. Plastics are composed of organic condensation or addition polymers and may contain other substances to improve performance or economics. In the claimed subject matter, plastic may comprise any one of the following forms of plastic: polyethylene, polystyrene, high impact polystyrene, polyethylene terephthalate, nylon, polypropylene, acrylonitrile butadiene styrene (ABS), bayblend and polyvinylidene chloride (PVC).

Figure 15:
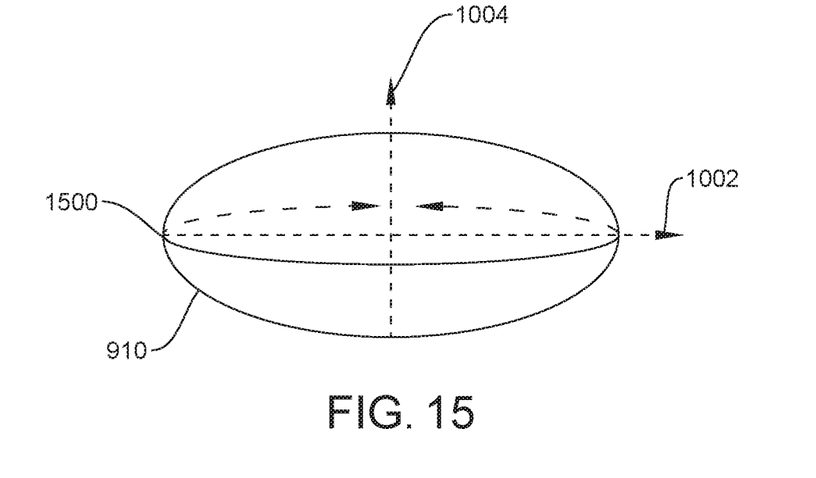
FIG. 15 is a side view of an improved balloon tamponade used for a kyphoplasty procedure, showing horizontal tension points, according to an example embodiment.
Figure 16:
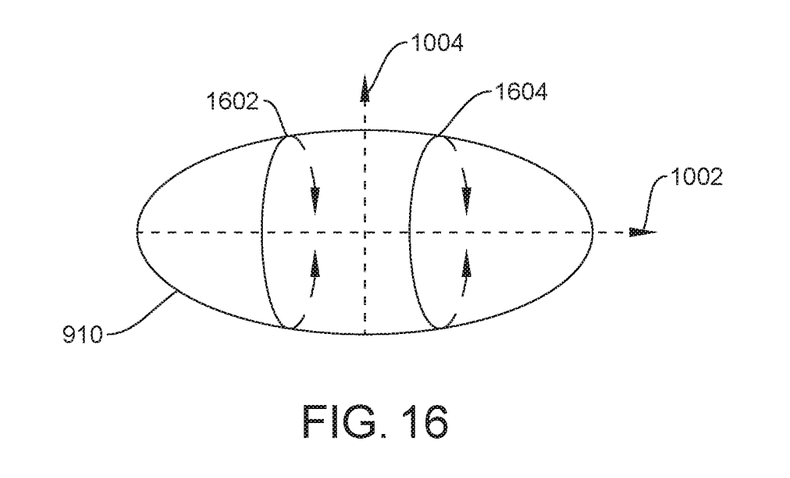
FIG. 16 is a side view of the improved balloon tamponade used for a kyphoplasty procedure, showing vertical tension points, according to an example embodiment.

FIGS. 15 and 16 are side views of the improved balloon tamponade 910 used for a kyphoplasty procedure, showing horizontal tension points 1500 and vertical tension points 1602, 1604, according to an example embodiment. FIG. 15 shows how the balloon tamponade 910 expands to a greater extent along the horizontal axis 1002, and to a lesser extent along the vertical axis 1004. The material used to make the balloon tamponade 910 includes vertical tension points 1602, 1604 that are much stronger and provide much more tension than the horizontal tension points 1500. Therefore, as the balloon tamponade 910 is inflated and the material of the balloon expands, the material will naturally expand to a greater extent along the horizontal axis 1002, and to a lesser extent along the vertical axis 1004. This results in the balloon tamponade 910 growing vertically, such that the vertebral cavity 910 is optimally filled from one trocar insertion only, as show in FIG. 13.

Put another way, FIGS. 15 and 16 shows the lateral deployment of the balloon tamponade 910, which expands horizontally (axis 1002), with respect to a vertical trocar (not shown). The balloon tamponade 910 is inflated such that, during deployment, it expands mainly along an axis 1002 that is orthogonal or perpendicular to a longitudinal axis of the trocar.

In another embodiment, the vertical tension points 1602, 1604 may comprise a continuous band of material that is deposited on top of (or underneath) the material of which the balloon tamponade 910 is constructed. In this embodiment, vertical tension points 1602, 1604 may comprise an elastic material (such as rubber) with an elasticity that is less than the elasticity of the remaining portions of the balloon tamponade 910, or with an elasticity that is less than the elasticity of the horizontal tension points 1500.

In yet another embodiment, the vertical tension points 1602, 1604 may comprise the same material of which the balloon tamponade 910 is constructed. In this embodiment, said material (of the vertical tension points 1602, 1604) may be thicker than the material of which the remainder of the balloon tamponade 910 is composed, or thicker than the material of which the horizontal tension points 1500 are composed.

Note that although only one set of horizontal tension points 1500 is disclosed and only two sets of vertical tension points 1602, 1604 are disclosed, the claimed embodiments support any number of horizontal tension points 1500 and vertical tension points 1602, 1604. Note also that although the horizontal tension points 1500 are disclosed as rings or bands around the balloon tamponade, the claimed embodiments support alternatives wherein the horizontal tension points 1500 cover or more areas of the balloon tamponade, such as a spherical sector, a conical boundary, a spherical cap or any other geometric shape on the surface of the balloon tamponade (including a circle, square, saddle, triangle, etc.). Note also that although the vertical tension points 1602, 1604 are disclosed as rings or bands around the balloon tamponade, the claimed embodiments support alternatives wherein the vertical tension points 1602, 1604 cover or more areas of the balloon tamponade, such as a spherical sector, a conical boundary, a spherical cap or any other geometric shape on the surface of the balloon tamponade.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

I claim:

1. A medical device for use in a kyphoplasty procedure, comprising:
    a) a trocar configured for insertion in a vertebral cavity, the trocar having a longitudinal axis that is perpendicular to a second axis that extends in a first direction and a second direction opposite the first direction;
    b) an orifice at a first end of the trocar, wherein the orifice is angled at an acute angle from the longitudinal axis, and wherein the orifice is configured for deploying a balloon tamponade;
    c) the balloon tamponade configured for inserting into a second end of the trocar, through the trocar and out of the orifice at the first end of the trocar wherein the balloon tamponade further includes: 1) horizontal tension points and vertical tension points, wherein the vertical tension points provide substantially more tension than the horizontal tension points, 2) at least one vertically aligned stripe of radiopaque material deposited on an exterior surface of the balloon tamponade and 3) at least one horizontally aligned stripe of radiopaque material deposited on the exterior surface of the balloon tamponade, wherein the at least one vertically aligned stripe is perpendicular to the at least one horizontally aligned stripe and wherein the at least one vertically aligned stripe intersects with the at least one horizontally aligned stripe; and
    d) wherein the balloon tamponade is configured to be inflated such that the balloon tamponade inflates to a greater extent along the second axis than the longitudinal axis of the trocar, wherein the balloon tamponade is configured to inflate entirely in the first direction of the second axis and the balloon tamponade does not inflate in the second direction of the second axis.

2. The medical device of claim 1, further comprising at least one vertically aligned stripe of radiopaque material deposited on an exterior surface of the balloon tamponade.

3. The medical device of claim 2, further comprising at least one horizontally aligned stripe of radiopaque material deposited on an exterior surface of the balloon tamponade.

4. The medical device of claim 3, wherein the balloon tamponade is composed of rubber.

5. The medical device of claim 4, wherein the balloon tamponade includes horizontal tension points and vertical tension points.

6. The medical device of claim 5, wherein the vertical tension points provide substantially more tension than the horizontal tension points.

7. A medical device for use in a kyphoplasty procedure, comprising:
    a) a trocar configured for insertion in a vertebral cavity, the trocar having a longitudinal axis that is perpendicular to a second axis that extends in a first direction and a second direction opposite the first direction;
    b) an orifice near a first end of the trocar, wherein the orifice is angled at an acute angle from the longitudinal axis, and wherein the orifice is configured for deploying a balloon tamponade;
    c) the balloon tamponade configured for inserting into a second end of the trocar, through the trocar and out of the orifice near the first end of the trocar wherein the balloon tamponade further includes: 1) horizontal tension points and vertical tension points, wherein the vertical tension points provide substantially more tension than the horizontal tension points, 2) at least one vertically aligned stripe of radiopaque material deposited on an exterior surface of the balloon tamponade and 3) at least one horizontally aligned stripe of radiopaque material deposited on the exterior surface of the balloon tamponade, wherein the at least one vertically aligned stripe is perpendicular to the at least one horizontally aligned stripe and wherein the at least one vertically aligned stripe intersects with the at least one horizontally aligned stripe; and
    d) wherein the balloon tamponade is configured to be inflated such that the balloon tamponade inflates to a greater extent along the second axis than the longitudinal axis of the trocar wherein the balloon tamponade is configured to inflate entirely in the first direction of the second axis and the balloon tamponade does not inflate in the second direction of the second axis.

8. The medical device of claim 7, further comprising at least one vertically aligned stripe of radiopaque material deposited on an exterior surface of the balloon tamponade.

9. The medical device of claim 8, further comprising at least one horizontally aligned stripe of radiopaque material deposited on an exterior surface of the balloon tamponade.

10. The medical device of claim 9, wherein the balloon tamponade is composed of rubber.

11. The medical device of claim 10, wherein the balloon tamponade includes horizontal tension points and vertical tension points.

12. The medical device of claim 11, wherein the vertical tension points provide substantially more tension than the horizontal tension points.

13. A medical device for use in a kyphoplasty procedure, comprising:
   a) a trocar configured for insertion in a vertebral cavity, the trocar having a longitudinal axis that is perpendicular to a second axis that extends in a first direction and a second direction opposite the first direction;
   b) an orifice near a first end of the trocar, wherein the orifice is angled at an acute angle from the longitudinal axis, and wherein the orifice is configured for deploying a balloon tamponade;
   c) the balloon tamponade configured for deploying out of the orifice near the first end of the trocar wherein the balloon tamponade further includes: 1) horizontal tension points and vertical tension points, wherein the vertical tension points provide substantially more tension than the horizontal tension points, 2) at least one vertically aligned stripe of radiopaque material deposited on an exterior surface of the balloon tamponade and 3) at least one horizontally aligned stripe of radiopaque material deposited on the exterior surface of the balloon tamponade, wherein the at least one vertically aligned stripe is perpendicular to the at least one horizontally aligned stripe and wherein the at least one vertically aligned stripe intersects with the at least one horizontally aligned stripe; and
   d) wherein the balloon tamponade is configured to be inflated such that the balloon tamponade inflates to a greater extent along the second axis than the longitudinal axis of the trocar, wherein the balloon tamponade is configured to inflate entirely in the first direction of the second axis and the balloon tamponade does not inflate in the second direction of the second axis.

14. The medical device of claim 13, further comprising at least one vertically aligned stripe of radiopaque material deposited on an exterior surface of the balloon tamponade.

15. The medical device of claim 14, further comprising at least one horizontally aligned stripe of radiopaque material deposited on an exterior surface of the balloon tamponade.

16. The medical device of claim 15, wherein the balloon tamponade is composed of rubber.

17. The medical device of claim 16, wherein the balloon tamponade includes horizontal tension points and vertical tension points.

18. The medical device of claim 17, wherein the vertical tension points provide substantially more tension than the horizontal tension points.

* * * * *